United States Patent
Sayles

[11] Patent Number: 6,074,606
[45] Date of Patent: *Jun. 13, 2000

[54] ONE-STEP TEST DEVICE

[76] Inventor: Philip W. Sayles, 172 Sycamore St., Watertown, Mass. 02472

[*] Notice: This patent is subject to a terminal disclaimer.

[21] Appl. No.: 09/175,042

[22] Filed: Oct. 19, 1998

[51] Int. Cl.$^7$ .............................. G01N 21/01; A61B 5/00
[52] U.S. Cl. .............................. 422/58; 422/61; 422/102; 604/404
[58] Field of Search .................................. 422/56, 58, 61, 422/100, 102, 103; 436/165; 604/404

[56] References Cited

U.S. PATENT DOCUMENTS

| | | | |
|---|---|---|---|
| 4,976,923 | 12/1990 | Lipsky et al. ............................. | 422/61 |
| 5,119,830 | 6/1992 | Davis ...................................... | 422/102 |
| 5,429,804 | 7/1995 | Sayles .................................... | 422/102 |
| 5,501,837 | 3/1996 | Sayles .................................... | 422/102 |
| 5,591,401 | 1/1997 | Sayles .................................... | 422/102 |
| 5,882,600 | 3/1999 | Davis ...................................... | 422/102 |

*Primary Examiner*—Jeffrey Snay
*Attorney, Agent, or Firm*—William Nitkin

[57] ABSTRACT

An improved test device for the testing of a fluid having a cup and a cover lid, such cover lid having a reagent test strip chamber containing a reagent test strip, a fluid receipt chamber, a fluid channel containing a fluid-passing pad and a fluid contact chamber. An actuation cover with a window defined therein is positioned over the regent test strip chamber, fluid receipt chamber, fluid contact chamber, such window positioned over the color change area of the reagent test strip. The actuation cover forms a fluid-tight seal around a first end of the reagent test strip which protrudes into the fluid contact chamber. After the cup is filled with fluid and the cover lid is positioned thereon, the cup is inverted, causing fluid to flow into the fluid receipt chamber through an aperture in said cover lid. When the test device is turned upright, the fluid drains from the bottom of the fluid receipt chamber, through the pad, down the fluid channel and into the fluid contact chamber where it comes in contact with the protruding first end of the reagent test strip, such fluid to be drawn along the reagent test strip to accomplish the desired test to cause the appropriate color change to appear on such reagent test strip visible through the window in the actuation cover. An actuation button on the actuation cover can aid in some embodiments to draw fluid into the fluid receipt chamber. In other embodiments a valve, when actuated, can open the fluid receipt chamber to receive the fluid to be tested when the cup is inverted.

3 Claims, 4 Drawing Sheets

ONE-STEP TEST DEVICE

BACKGROUND OF THE INVENTION

1. Field of the Invention

The device of this invention resides in the area of structures for the conducting of chromatographic immunoassay testing of a fluid on a reagent-containing membrane strip and more particularly relates to a test container holding the fluid to be tested to accomplish a test while the container is in a closed state.

2. Description of the Prior Art

Triage assay testing of bodily fluids is well known but has the serious disadvantage of requiring the tester to be exposed to contact with bodily fluids, such as urine, during the pipetting step. Such tests are slow, multi-step procedures which are difficult to carry out in hectic environments such as hospital emergency rooms.

In the prior art is U.S. Pat. No. 4,976,923 to Lipsky et al which patent discloses a specimen cup with a cover wherein the fluid to be tested is first placed in the specimen cup. The cover is positioned on the cup, and the closed cup is inverted so that the fluid can pass into apertures in the cover assembly where it reacts with a reagent therein to cause different color reactions which display the analytical characteristics of the fluid being tested. Such a specimen cup structure has great advantages in today's health environment where bodily fluids may contain dangerous viruses such as AIDS and the like. Health workers do not want to endanger their health by coming in direct physical contact with such fluids but still wish to perform necessary tests safely. In some cases the sealing of the fluids within such a specimen cup can be done by the person whose fluids are being tested. For example, in urine testing the subject whose urine is to be tested would urinate into the specimen cup and would then place the cover on the cup, sealing the urine in the cup. The lab technician performing the test need not open the cup or come in direct contact with the bodily fluids contained in the specimen cup. Thus a specimen cup which can be sealed during testing has a significant advantage over the open-cup fluid testing procedures of the past. U.S. Pat. No. 5,119,830 to Davis advances this concept in the prior art by providing a test space in the lid, under a transparent top, for positioning chemical test strip pads, such test space being initially sealed and when desired, a frangible portion of the inside of the lid can be broken open by pressure through the top of the lid to allow fluid to flood into the test space when the cup is inverted and cover the pads, the color change of which is visible through the transparent top of the test chamber.

SUMMARY OF THE INVENTION

It is an object of this invention to provide improvements to my One-step Test Device taught by my U.S. Pat. No. 5,591,401 issued Jan. 7, 1997. The invention disclosed herein provides for an improved entry of fluids into the chamber system.

It is a general goal of this invention to provide an improved closed specimen cup testing system utilizing a cover lid containing a reagent membrane strip for the efficient conducting of chromatographic immunoassay testing. Chromatographic immunoassay strips cannot work if totally immersed in the fluid to be tested but must contact such fluid only at one end portion so that the fluid can be drawn along the strip by capillary action.

The structure of this invention in one embodiment provides for a cup, a cover lid, a reagent test strip chamber and fluid receipt chamber, the latter two disposed within the cover lid. A reagent test strip is positioned in the reagent test strip chamber. One end of the reagent test strip extends through an opening formed by the lid and the actuation cover and protrudes into a fluid contact chamber where such reagent test strip's protruding end can come into contact with the fluid to be tested while at the same time preventing such fluid from contacting or flooding over or under the balance of such strip. In its test mode, the lid is closed, as described below, and the cup is inverted. The fluid to be tested passes through an opening into the fluid receipt chamber and fills it with a specific amount of fluid. The cup is then turned upright, and the fluid in such specified amount pools in the fluid receipt chamber and passes through a fluid channel absorbed through a nitrocellulose pad where such fluid enters into the fluid contact chamber and then contacts only the end of the reagent test strip that is protruding into the fluid contact chamber. The fluid is then drawn along the reagent test strip to the strip's color change area. The color change area of the reagent test strip is visible through an elongated open window formed in the actuation cover.

In test mode use, when the fluid specimen is placed within the specimen cup and the cover lid is affixed in fluid-tight relationship thereon such as by screw threads or other attachment means, the fluid receipt chamber is opened to the inside of the cup, as more fully described below, and the specimen cup is inverted, allowing a predetermined amount of the fluid to be tested to enter the fluid receipt chamber. When the cup is turned upright, the fluid collects in the bottom of the fluid receipt chamber where it pools and passes through the fluid channel to the nitrocellulose pad and thereon to the fluid contact chamber where it comes in contact with the protruding first end of the reagent test strip which extends out of an opening in the reagent strip chamber. The fluid is drawn along the reagent test strip toward the center of the reagent strip chamber by capillary action until the fluid comes to the bands of the chromatographic immunoassay test reagent where a color change can occur to perform the desired test. Very small amounts of the fluid sample are carried by such capillary action from the fluid contact chamber along the length of the reagent strip. An opening forming a window in the actuation cover on the top of the cover lid disposed immediately above the reagent strip allows the visible color change area of the reagent strip to be observed for color change reactions, and a label or indicia adjacent to such open window can identify the test such reagent strip is performing. The testing device of this invention combines all the advantages of a closed container test system for fluids, such as urine and the like, and provides for a uniform measured quantity of fluid to be tested to be positioned at the end of the reagent test strip.

DESCRIPTION OF THE PREFERRED EMBODIMENT(S)

Figure 1:
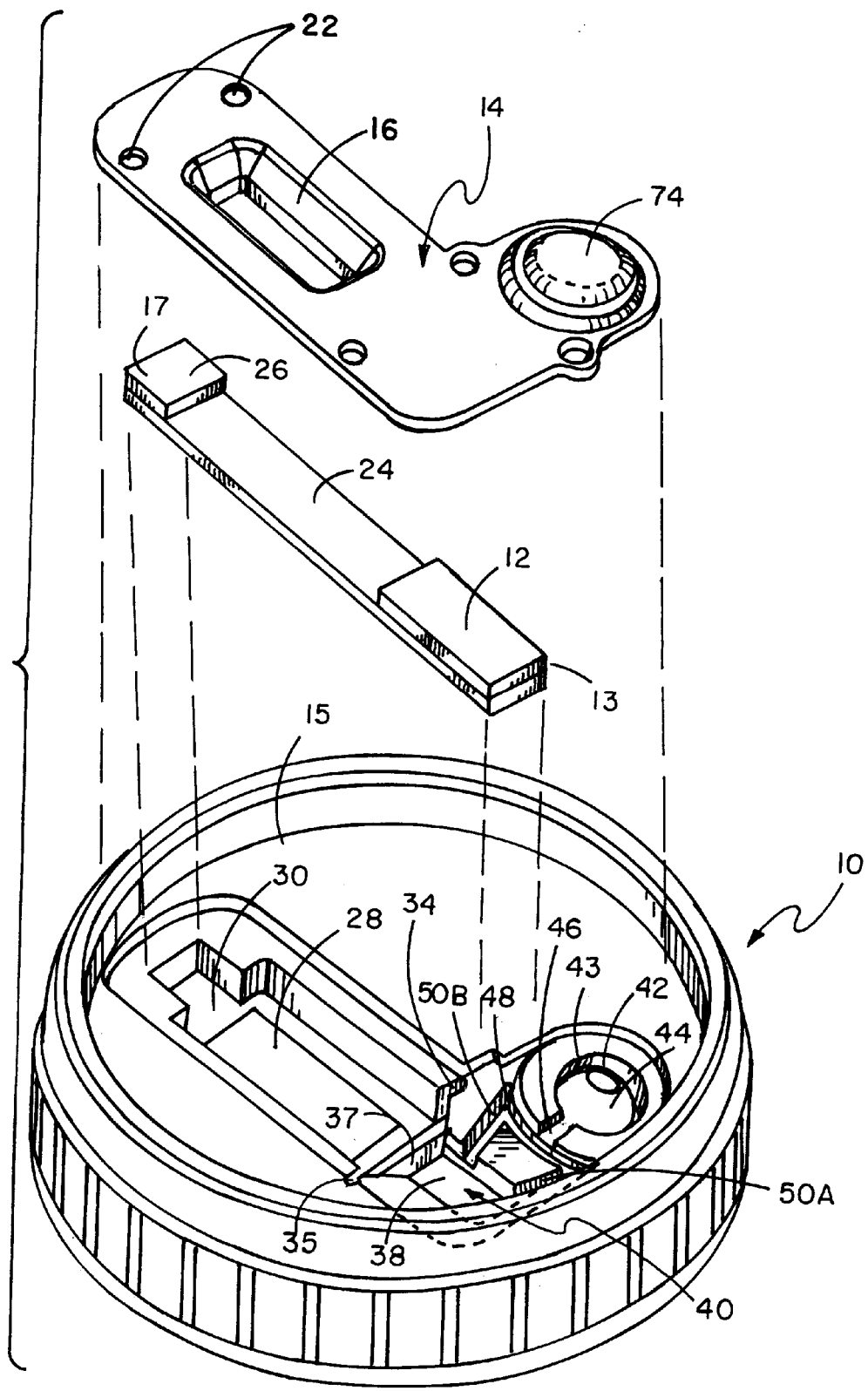
FIG. 1 illustrates a perspective top view of the cover lid of the test device of this invention showing the reagent test strip chamber, fluid receipt chamber, fluid channel and fluid contact chamber, with the actuation cover and reagent test strip removed and shown thereabove.
Figure 2:
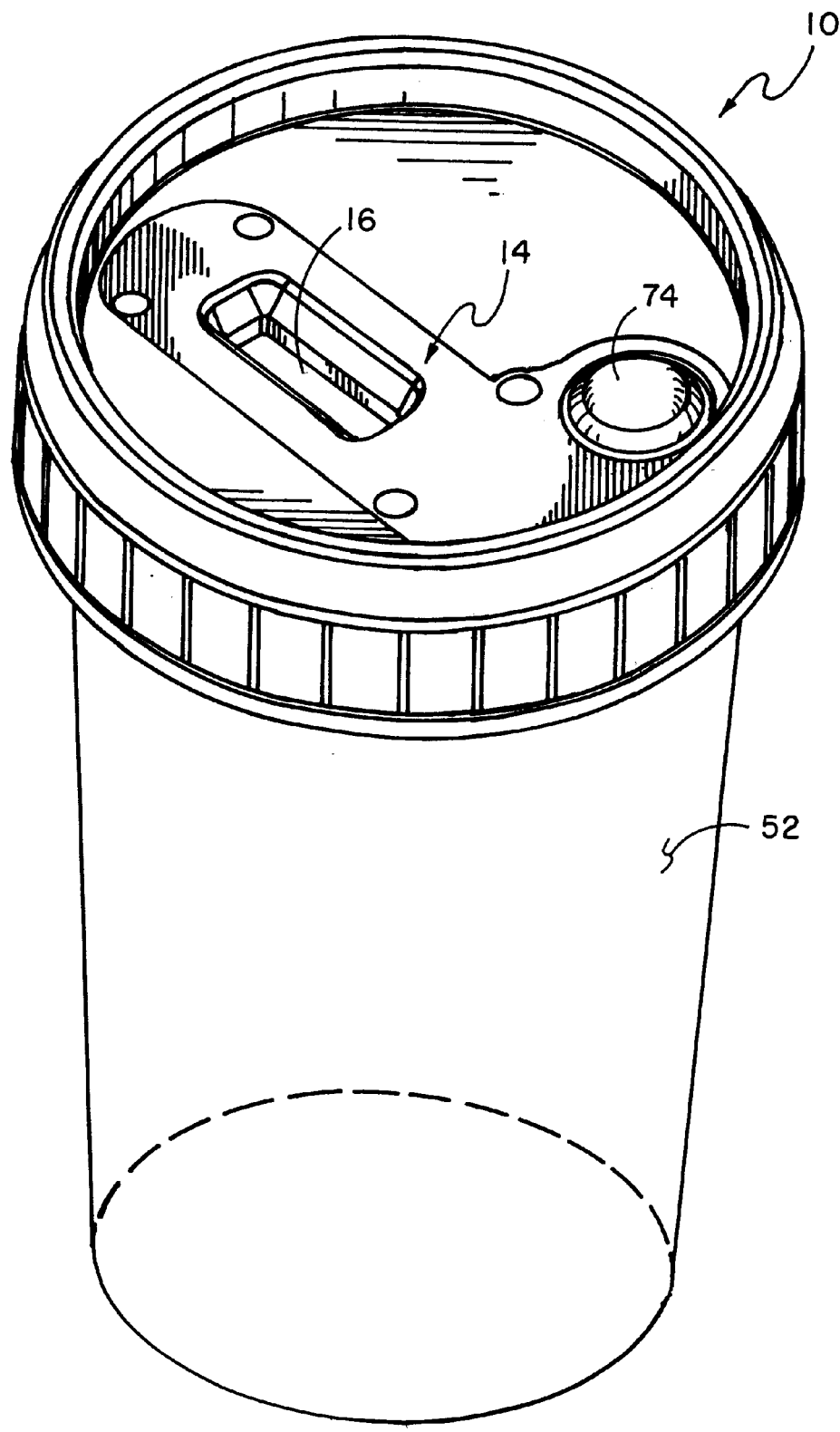
FIG. 2 illustrates a perspective view of the cover lid disposed on a specimen cup.
Figure 3:
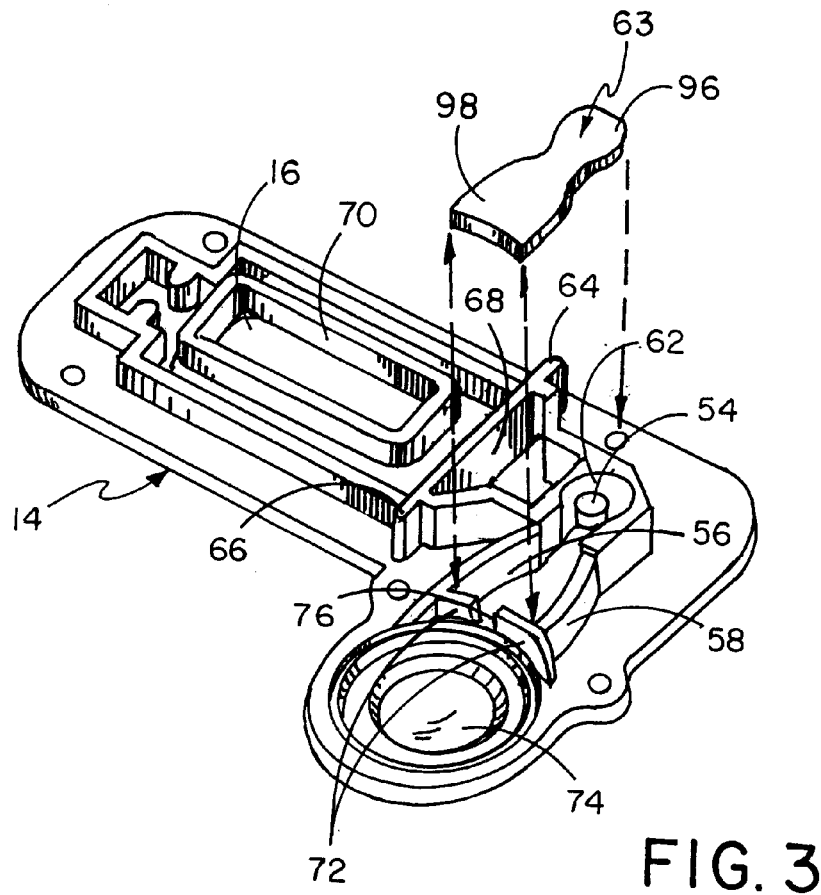
FIG. 3 illustrates a perspective bottom view of an actuation cover and also showing the nitrocellulose pad separated therefrom.

FIG. 1 illustrates a perspective view of cover lid 10, having a top and bottom, of the fluid testing device of this invention. Not shown in this view, but seen in FIG. 2, is the specimen cup in which cup the fluid to be tested would be deposited, such specimen cup being well known. The cover lid can be attached to the cup by screw-on threads disposed at the outer top surface of the cup which threads would interengage in fluid-tight relationship with mating threads disposed on the inner side of the cover lid side wall. Other means of fluid-tight attachment of the cover lid to the cup, such as snap-on friction-fit, can also be used as long as such means securely holds the cover lid onto the cup when the testing device is inverted for the fluid to enter the fluid receipt chamber, as described below. In actuation cover 14, as seen in FIG. 1, shown above cover lid 10 is defined open window 16 immediately above the visible color change area of reagent test strip 24. Indicia can be printed on the cover lid's top surface or actuation cover's top surface to indicate the particular test being performed on the reagent test strip. L-shaped actuation cover 14 is permanently affixed to the top of cover lid 10 and has actuation button 74 thereon. Cover lid 10 can be formed of a plastic molded lower lid 15 in which can be placed the reagent test strip 24 and onto which lower lid actuation cover 14, which can also be made of plastic, can then be permanently affixed. Several chambers can be formed in lower lid 15 during its molding. Reagent test strip chamber 28 can be formed to receive reagent test strip 24, as seen disposed thereabove, the first end 12 of which will protrude into fluid contact chamber 40. Reagent test strip chamber 28 extends to fluid contact chamber 40 where its first end 12 is held in reagent strip first end receipt area 38. Fluid receipt chamber 43 is disposed at approximately a 90-degree angle to reagent test strip chamber 28, forming an L shape. When reagent test strip 24 is positioned in reagent test strip chamber 28, its first end 12 extends beyond first and second rib receipt openings 34 and 35 on each side thereof into fluid contact chamber 40. As seen in FIG. 3, which is a perspective bottom view of actuation cover 14, first rib member 66 and second rib member 64 are positioned to mate, respectively, into first and second rib receipt openings 34 and 35 to form a seal around protruding first end 12 of reagent test strip 24 with wall 68 of actuation cover 14 forming a fluid-tight seal around reagent test strip 24 and with protruding end 12 extending into fluid contact chamber 40. A depression 37, seen in FIG. 1, can be provided in the floor of fluid contact chamber 40 to form a "gate" to help prevent any capillary action from occurring too quickly with fluid that may have been drawn between the reagent test strip chamber's floor and the reagent test strip. The use of such a "gate" is known in the art to be helpful when using reagent test strips which rest on surfaces. As can be seen in FIG. 3, actuation cover 14 has window 16, the side walls 70 of which extend inward to contact, and help retain, the reagent test strip in place, such window being disposed directly above the color change area to be viewed on the reagent test strip. The structures of the actuation cover and cover lid interact to retain the color change area of the reagent test strip in an area that cannot be contacted directly by fluid except through first end 12 of reagent test strip 24 which extends into fluid contact chamber 40 and thus prevents any fluid from escaping to the outer environment through window 16. Actuation cover 14 can be permanently attached to lower lid 15 by gluing, ultrasonic welding such as at points 22 or equivalent means of attachment. Disposed at one end of actuation cover 14 is depressible actuation button 74. Once actuation cover 14 is permanently positioned on cover lid 10 over reagent test strip 24, as seen in FIG. 2, and the cup inverted, fluid deposited within cup 52 can flow into fluid receipt chamber 43 through aperture 42 formed in lower lid 15. The large volume of the deposited fluid sample in the cup, when the cup is inverted, creates sufficient pressure on the fluid to cause it to pass through aperture 42 to fill fluid receipt chamber 43. When the cup is reverted and the deposited fluid falls back to the bottom of cup 52, the fluid that has flowed into fluid receipt chamber 43 is of insufficient volume to create enough pressure to flow back out through aperture 42. In some embodiments, activation button 74 can be utilized to aid in filling the fluid receipt chamber with fluid. When the entire lid cup structure is inverted, one can depress actuation button 74 and let it pop back up to its original position, which action creates a negative air pressure or slight vacuum thereunder which pulls the fluid through aperture 42 into fluid receipt chamber 43. Aperture 42 can be of a small size, having a diameter in the range of 0.020 inch to 0.040 inch for fluid to pass therethrough. As mentioned above, when the cup is then turned upright, the fluid that has been drawn into fluid receipt chamber 43 remains in such chamber and does not pass back out through aperture 42 as there is insufficient pressure to force the fluid out through such small aperture.

Figure 5:
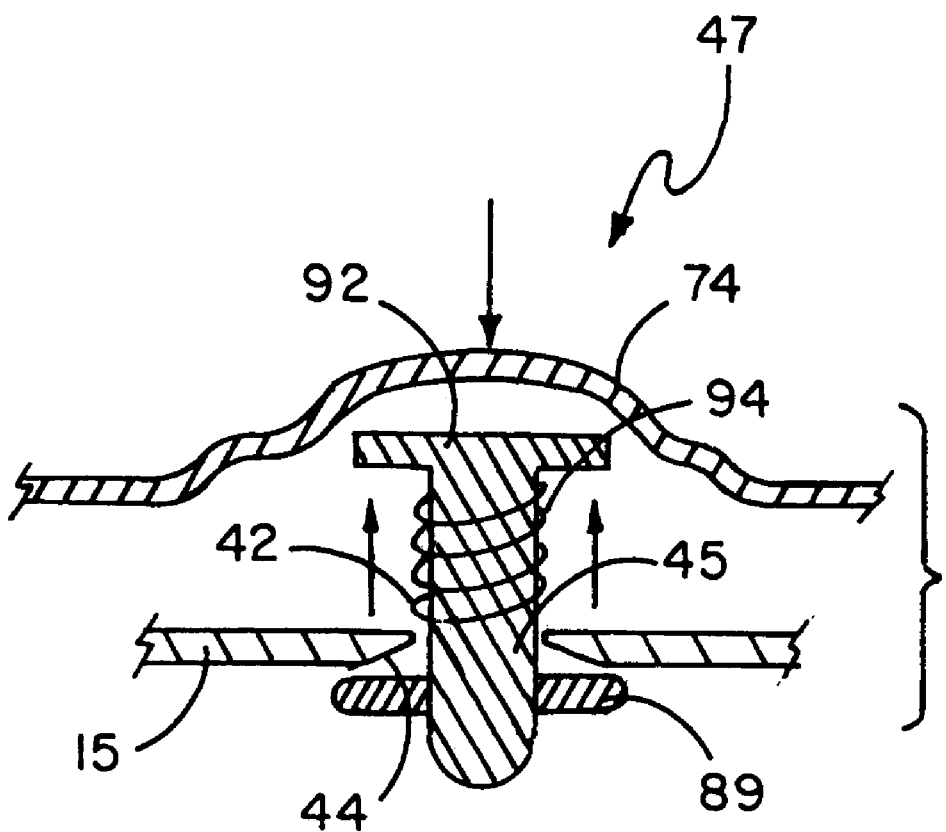
FIG. 5 illustrates a cross-sectional view through a valve in the cover lid.

In an alternate embodiment, a valve 47 disposed immediately under actuation button 74, seen in cross-section in FIG. 5, can be used. In this view a T-shaped member 92 passes through aperture 42 and has a sealing washer 89 affixed therearound. A spring member 94 keeps the T-shaped member 92 and attached sealing washer 89 tightly against beveled area 44 defined in the bottom of lid 15 around aperture 42. When valve 47 is closed, spring 94 pushes the top of T-shaped member 92 upwards so that attached sealing washer 89 fills beveled area 44 and contacts the bottom of lower lid 15 in a fluid-tight fashion. Upon inversion of cup 52, one can depress actuation button 74, thereby pushing T-shaped member 92 of valve 47 against the action of spring 94 and thereby moving sealing washer 89 out of beveled area 44 and opening space 45 defined between the body of T-shaped member 92 and the sides of aperture 42 through which the fluid can pass into fluid receipt chamber 43.

As seen in FIGS. 1 and 3, when the cup is turned upright, the fluid flows down the sloped bottom of fluid receipt chamber 43 to its edges where the fluid passes from fluid receipt chamber 43 through slot 76 aligned with channel 46 and comes in contact with first end 98 of a fluid-passing pad such as nitrocellulose pad 63 where it is drawn through pad 63 into fluid contact chamber 40. The fluid that has passed through nitrocellulose pad 63 to fluid contact chamber is then drawn by capillary action from second end 96 of nitrocellulose pad 63 into the test strip absorbent pad 13 with which it makes contact and then along reagent test strip 24 to the area under test window 16 where the test results can be observed. Fluid receipt chamber 43 has fluid receipt chamber wall member slot 48 disposed around a portion thereof which receives fluid receipt chamber wall member 72 formed as part of actuation cover 14. Extending from the ends of the fluid receipt chamber wall member 72 are first and second fluid channel wall members 56 and 58 which partially contain nitrocellulose pad 63 and further engage to, and mate with, respectively, first and second fluid channel wall member receipt slots 50B and 50A. First and second fluid channel wall members 56 and 58 aid in directing the fluid from the higher positioned fluid receipt chamber 43 down through slot 76 in fluid receipt chamber wall member 72 into contact with nitrocellulose pad 63 and hence into fluid contact chamber 40. At the other ends of the first and second fluid channel wall members 56 and 58 is defined a fluid contact chamber wall member 62 which is circular and helps direct and retain the fluid in the fluid contact chamber 40 above first end 12 of reagent test strip 24. Protrusion 54 helps maintain contact between second end 96 of nitrocellulose pad 63 and test strip absorbent pad 13 of reagent test strip 24. Reagent test strip 24 at its first end 12 has test strip absorbent pad 13 which makes contact with nitrocellulose pad 63 and fluid contact chamber wall member 62. Also contacting test strip absorbent pad 13 is wall 68. The fluid is absorbed by test strip absorbent pad 13 and is drawn by capillary action along reagent test strip 24. A second absorbent pad 17 is disposed at the second end 26 of the reagent test strip and aids in helping to draw fluid to that end of reagent test strip 24.

Figure 4:
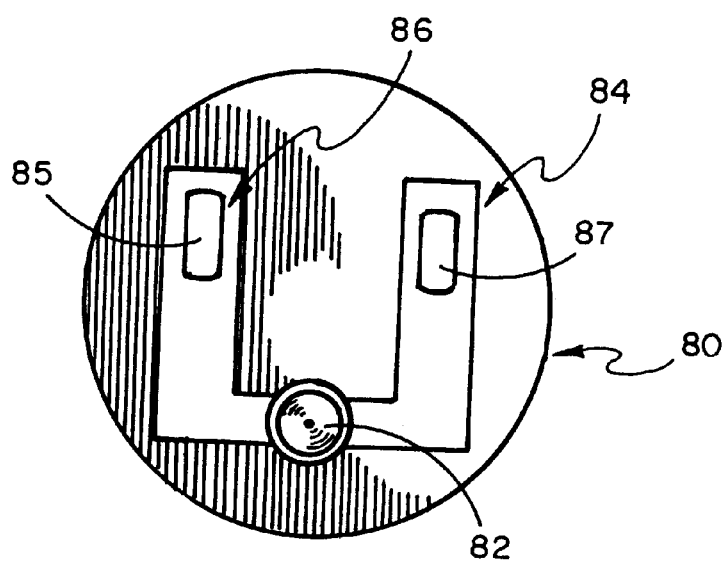
FIG. 4 illustrates a top plan view of an alternate embodiment of the device of this invention showing the cover lid with two reagent strip chambers extending from the same fluid receipt chamber.

FIG. 4 illustrates an alternate embodiment of this invention having two reagent test strip chambers extending from the same fluid receipt chamber, not shown. The fluid receipt chamber is located under central actuation button 82 wherein first and second fluid receipt chambers 84 and 86 having, respectively, first and second test strip chambers and first and second windows 87 and 85 fit within lid 80 in a U-shaped configuration with each reagent test strip chamber having its own fluid receipt chamber fluid channel and nitrocellulose pad disposed therein.

Although the present invention has been described with reference to particular embodiments, it will be apparent to those skilled in the art that variations and modifications can be substituted therefor without departing from the principles and spirit of the invention.

What is claimed is:

1. An improved one-step test device having a test mode, said device having a cup for receipt of a fluid specimen to be tested and a cover lid having a top and bottom, said cover lid to be attached to said cup in a fluid-tight relationship, comprising:

a reagent test strip chamber defined in said top of said cover lid, said reagent test strip chamber having a floor and first and second sides formed from said cover lid;

a fluid receipt chamber having a bottom formed from said cover lid;

a fluid channel formed in said cover lid, said cover lid including first and second fluid channel walls;

a fluid contact chamber formed in said cover lid including a wall in said cover lid interconnected with said first and second fluid channels walls;

an absorbent pad positioned in said fluid channel between said first and second fluid channel walls, said absorbent pad drawing fluid therethrough, a portion of said absorbent pad extending into said fluid contact chamber;

a reagent test strip positioned in said reagent test strip chamber, said reagent test strip having a first end having a test strip absorbent pad thereon, a second end having a second test strip absorbent pad thereon, a top, sides, and a color change testing area disposed between said first and second ends, said first end of said reagent test strip disposed in said fluid contact chamber with said first test strip absorbent pad in contact with said portion of said absorbent pad in said fluid contact chamber;

means to maintain contact between said absorbent pad and said first test strip absorbent pad;

an actuation cover having a top and a bottom, said actuation cover covering said reagent test strip chamber, said fluid channel, said fluid contact chamber and said fluid receipt chamber, said actuation cover further including downwardly extending side walls disposed around said color change testing area of said reagent test strip, said side walls for sandwiching said reagent test strip between said side walls and said floor of said reagent test strip chamber and helping to retain said reagent test strip in said reagent test strip chamber and further helping to prevent the escape of any fluid therefrom;

an actuation button formed in said actuation cover disposed over said fluid receipt chamber;

means to prevent said fluid from passing from said fluid contact chamber into said reagent test strip chamber, said means allowing for said first end of said reagent test strip to extend from said reagent test strip chamber and to protrude into said fluid contact chamber, said means comprising:

first and second slots defined, respectively, in said first and second sides of said reagent test strip chamber;

a wall having a first and second end, said wall disposed at said bottom of said actuation cover; and first and second rib members disposed at said bottom of said actuation cover extending beyond said first and second ends of said wall, said first and second rib members positioned to mate, respectively, into said first and second slots, said wall and rib members to surround the top and sides of said reagent test strip in a fluid-tight relationship, allowing said first end of said reagent test strip to be positioned in said fluid contact chamber while the balance of said reagent test strip is protected from contact with said fluid;

an aperture defined in said cover lid in the bottom of said fluid receipt chamber;

a valve disposed in said aperture, said valve for opening and closing said aperture, respectively, by the depression and subsequent release of said actuation button;

said test device, when said cover lid is positioned on a fluid-filled cup and said cup is inverted, allowing fluid into said fluid receipt chamber through said aperture upon depressing and stopping the flow of fluid upon releasing said actuation button, said test device when said cup is turned upright, allowing said fluid to drain from said fluid receipt chamber down said fluid channel through said absorbent pad and into said fluid contact chamber to come in contact with said first test strip absorbent pad at said first end of said reagent test strip to cause said fluid to be carried along said reagent test strip to said color change testing area; and a window defined in said actuation cover within said side walls, said window disposed above said color change testing area, through which window the test results can be viewed.

2. The test device of claim 1 wherein said fluid receipt chamber is disposed at approximately a right angle to said reagent test strip chamber and said actuation cover is formed in an L shape, said actuation cover being permanently affixed to said cover lid disposed above said reagent test strip chamber, said fluid receipt chamber, said fluid channel and said fluid contact chamber.

3. The test device of claim 2 further including:

a second fluid channel formed in said cover lid;

a second fluid contact chamber formed in said cover lid;

a second reagent test strip chamber defined in said top of said cover lid, said reagent test strip chamber having a floor and first and second sides formed from said cover lid;

a second reagent test strip positioned in said second reagent test strip chamber, said second reagent test strip having a first end, a second end, a top, sides, and a color change testing area disposed between its first and second ends, said first end of said second reagent test strip disposed in said fluid contact chamber in contact with said portion of said absorbent pad in said fluid contact chamber; and a second window defined in said actuation cover, said second window disposed above its respective color change testing area through which second window test results can be viewed.

* * * * *